(12) United States Patent
Tamarkin et al.

(10) Patent No.: US 8,119,106 B2
(45) Date of Patent: Feb. 21, 2012

(54) FOAMABLE IODINE COMPOSITIONS

(75) Inventors: Dov Tamarkin, Maccabim (IL); Doron Friedman, Karmei Yosef (IL); Meir Eini, Ness Ziona (IL)

(73) Assignee: Foamix Ltd, Rehovot (IL)

( * ) Notice: Subject to any disclaimer, the term of this patent is extended or adjusted under 35 U.S.C. 154(b) by 27 days.

(21) Appl. No.: 12/499,609

(22) Filed: Jul. 8, 2009

(65) Prior Publication Data

US 2009/0317338 A1 Dec. 24, 2009

Related U.S. Application Data

(62) Division of application No. 10/835,359, filed on Apr. 28, 2004, now Pat. No. 7,575,739.

(60) Provisional application No. 60/466,094, filed on Apr. 28, 2003.

(51) Int. Cl.
*A61K 9/00* (2006.01)
*A61K 9/12* (2006.01)
*A61K 33/18* (2006.01)

(52) U.S. Cl. ......... 424/45; 424/400; 424/51; 424/78.06; 424/78.07; 514/945; 514/928; 514/887; 514/828

(58) Field of Classification Search .................... 424/45, 424/400, 51, 78.06, 78.07; 514/945, 928, 514/887, 828
See application file for complete search history.

(56) References Cited

U.S. PATENT DOCUMENTS

| | | |
|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,968,628 A | 1/1961 | Reed |
| 3,062,715 A | 11/1962 | Reese |
| 3,067,784 A | 12/1962 | Gorman |
| 3,092,255 A | 6/1963 | Hohman |
| 3,395,214 A | 10/1963 | Schramm et al. |
| 3,141,821 A | 7/1964 | Compeau |
| 3,142,420 A | 7/1964 | Gawthrop |
| 3,144,386 A | 8/1964 | Brighttenback |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienciewicz |
| 3,263,869 A | 8/1966 | Corsette |
| 3,298,919 A | 1/1967 | Bishop et al. |
| 3,301,444 A | 1/1967 | Wittke |
| 3,527,559 A | 1/1967 | Sliwinski |
| 3,303,970 A | 2/1967 | Breslau et al. |
| 3,330,730 A | 7/1967 | Hemaadez |
| 3,346,451 A | 10/1967 | Collins et al. |
| 3,369,034 A | 2/1968 | Chalmers |
| 3,384,541 A | 5/1968 | Clark et al. |
| 3,395,215 A | 7/1968 | Warren |
| 3,401,849 A | 9/1968 | Weber, III |
| 3,419,658 A | 12/1968 | Amsdon |
| 3,559,890 A | 2/1971 | Brooks et al. |
| 3,561,262 A | 2/1971 | Borocki |
| 3,574,821 A | 4/1971 | Pfirrmann et al. |
| 3,577,518 A | 5/1971 | Shepherd |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,849,580 A | 11/1974 | Sejpal et al. |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,959,160 A | 5/1976 | Horsler et al. |
| 3,962,150 A | 6/1976 | Viola |
| 3,963,833 A | 6/1976 | DeSalva et al. |
| 3,966,090 A * | 6/1976 | Prussin et al. .................. 222/94 |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |

(Continued)

FOREIGN PATENT DOCUMENTS

AU 198780257 9/1986

(Continued)

OTHER PUBLICATIONS

Disorder. (2007). In the American Heritage® Dictionary of the English Language. Retrieved from http://www.credoreference.com/entry/hmdictenglang/disorder.*

(Continued)

*Primary Examiner* — Mina Haghighatian
(74) *Attorney, Agent, or Firm* — Wilmer Cutler Pickering Hale and Dorr LLP

(57) ABSTRACT

The present invention is related to a foamable composition of matter comprising iodine, water, a foam adjuvant, a surface-active agent and a gelling agent. This foamable composition, which may be provided in a propellant free foaming device, or alternatively may further comprise a propellant, evolves into foam, which is effective in the topical treatment and prevention of various skin disorders.

25 Claims, 1 Drawing Sheet

U.S. PATENT DOCUMENTS

| | | |
|---|---|---|
| 3,997,467 A | 12/1976 | Jederstrom |
| 4,001,391 A | 1/1977 | Feinstone et al. |
| 4,001,442 A | 1/1977 | Stahlberger et al. |
| 4,019,657 A | 4/1977 | Spitzer et al. |
| 4,102,995 A | 7/1978 | Hebborn |
| 4,110,426 A | 8/1978 | Barnhurst |
| 4,124,149 A | 11/1978 | Spitzer et al. |
| 4,145,411 A | 3/1979 | Mende |
| 4,160,827 A | 7/1979 | Cho et al. |
| 4,213,979 A | 7/1980 | Levine |
| 4,214,000 A | 7/1980 | Papa |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,310,510 A | 1/1982 | Sherman et al. |
| 4,323,694 A | 4/1982 | Scala, Jr. |
| 4,335,120 A | 6/1982 | Holick et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,439,416 A | 3/1984 | Cordon et al. |
| 4,439,441 A | 3/1984 | Hallesy et al. |
| 4,447,486 A | 5/1984 | Hoppe et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,627,973 A | 12/1986 | Moran |
| 4,628,063 A | 12/1986 | Haines et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,741,855 A | 5/1988 | Grote et al. |
| 4,752,465 A | 6/1988 | Mackles |
| 4,770,634 A | 9/1988 | Pellico |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior |
| 4,806,262 A | 2/1989 | Snyder |
| 4,808,388 A | 2/1989 | Beutler et al. |
| 4,822,613 A | 4/1989 | Rodero |
| 4,827,378 A | 5/1989 | Gillan et al. |
| 4,828,837 A | 5/1989 | Uster et al. |
| 4,836,217 A | 6/1989 | Fischer |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,855,294 A | 8/1989 | Patel et al. |
| 4,863,900 A | 9/1989 | Pollock et al. |
| 4,867,967 A * | 9/1989 | Crutcher ............... 424/78.05 |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,906,453 A | 3/1990 | Tsoucalas |
| 4,913,893 A | 4/1990 | Varco et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,970,067 A | 11/1990 | Panandiker et al. |
| 4,975,466 A | 12/1990 | Bottcher et al. |
| 4,981,677 A | 1/1991 | Thau |
| 4,981,679 A | 1/1991 | Briggs et al. |
| 4,981,845 A | 1/1991 | Pereira |
| 4,992,478 A | 2/1991 | Geria |
| 5,002,540 A | 3/1991 | Brodman et al. |
| 5,002,680 A | 3/1991 | Schmidt et al. |
| 5,007,556 A | 4/1991 | Lover |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs et al. |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo |
| 5,384,308 A | 1/1995 | Henkin |
| 5,385,943 A | 1/1995 | Nazzaaro-Porro |
| 5,389,676 A | 2/1995 | Michaels |
| 5,397,312 A | 3/1995 | Rademaker et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |

| Patent No. | Date | Name |
|---|---|---|
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,603,940 A | 2/1997 | Candau et al. |
| 5,605,679 A | 2/1997 | Hansenne et al. |
| 5,611,463 A | 3/1997 | Favre |
| 5,612,056 A | 3/1997 | Jenner et al. |
| 5,614,171 A | 3/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,650,554 A | 7/1997 | Moloney |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,695,551 A | 12/1997 | Buckingham et al. |
| 5,700,396 A | 12/1997 | Suzuki et al. |
| 5,716,611 A * | 2/1998 | Oshlack et al. ............ 424/78.25 |
| 5,719,122 A | 2/1998 | Chiodini et al. |
| 5,719,197 A | 2/1998 | Kanios et al. |
| 5,725,872 A | 3/1998 | Stamm et al. |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,759,520 A | 6/1998 | Sachetto |
| 5,759,579 A | 6/1998 | Singh et al. |
| 5,767,104 A | 6/1998 | Bar-Shalom et al. |
| 5,783,202 A | 7/1998 | Tomlinson et al. |
| 5,792,448 A | 8/1998 | Dubief et al. |
| 5,792,922 A | 8/1998 | Moloney et al. |
| 5,804,546 A | 9/1998 | Hall |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn |
| 5,849,042 A | 12/1998 | Lim et al. |
| 5,856,452 A | 1/1999 | Moloney et al. |
| 5,858,371 A | 1/1999 | Singh et al. |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,885,581 A | 3/1999 | Massand |
| 5,889,028 A | 3/1999 | Sandborn et al. |
| 5,891,458 A | 4/1999 | Britton |
| 5,902,574 A | 5/1999 | Stoner et al. |
| 5,902,789 A | 5/1999 | Stoltz |
| 5,905,092 A | 5/1999 | Osborne et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,922,331 A | 7/1999 | Mausner |
| 5,948,682 A | 9/1999 | Moloney |
| 5,951,993 A | 9/1999 | Scholz et al. |
| 5,952,373 A | 9/1999 | Lanzendorfer et al. |
| 5,952,392 A | 9/1999 | Katz et al. |
| 5,961,957 A | 10/1999 | McAnalley |
| 5,972,310 A | 10/1999 | Sachetto |
| 5,976,555 A | 11/1999 | Liu et al. |
| 5,980,904 A | 11/1999 | Leverett et al. |
| 5,993,846 A | 11/1999 | Friedman et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,071,536 A | 6/2000 | Suzuki et al. |
| 6,075,056 A | 6/2000 | Quigley, Jr. et al. |
| 6,080,394 A | 6/2000 | Lin et al. |
| 6,087,317 A | 7/2000 | Gee |
| 6,090,772 A | 7/2000 | Kaiser et al. |
| 6,093,408 A | 7/2000 | Hasenoehrl et al. |
| 6,110,477 A | 8/2000 | Hernandez et al. |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,221,381 B1 | 4/2001 | Shelford et al. |
| 6,224,888 B1 | 5/2001 | Vatter |
| 6,231,837 B1 | 5/2001 | Stroud et al. |
| 6,232,315 B1 | 5/2001 | Shafer et al. |
| 6,251,369 B1 | 6/2001 | Stoltz |
| 6,258,374 B1 | 7/2001 | Friess et al. |
| 6,271,295 B1 | 8/2001 | Powell et al. |
| 6,274,150 B1 | 8/2001 | Simonnet et al. |
| 6,287,546 B1 | 9/2001 | Reich et al. |
| 6,294,550 B1 | 9/2001 | Place |
| 6,299,023 B1 | 10/2001 | Arnone |
| 6,299,900 B1 | 10/2001 | Reed et al. |
| 6,305,578 B1 | 10/2001 | Hildebrandt et al. |
| 6,306,841 B1 | 10/2001 | Place |
| 6,308,863 B1 | 10/2001 | Harman |
| 6,319,913 B1 | 11/2001 | Mak et al. |
| 6,328,950 B1 | 12/2001 | Franzke et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,358,541 B1 | 3/2002 | Goodman |
| 6,372,234 B1 | 4/2002 | Deckers et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,455,076 B1 | 9/2002 | Hahn et al. |
| 6,468,989 B1 | 10/2002 | Chang et al. |
| 6,479,058 B1 | 11/2002 | McCadden |

| Patent/Pub No. | Date | Inventor |
|---|---|---|
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,536,629 B2 | 3/2003 | van der Heijden |
| 6,544,530 B1 | 4/2003 | Friedman |
| 6,548,074 B1 | 4/2003 | Mohammadi |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy et al. |
| 6,682,726 B2 | 1/2004 | Marchesi et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,753,000 B2 | 6/2004 | Breton et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,890,567 B2 | 5/2005 | Nakatsu et al. |
| 6,902,737 B2 | 6/2005 | Quemin |
| 6,911,211 B2 | 6/2005 | Eini et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Brandt et al. |
| 6,967,023 B1 | 11/2005 | Eini et al. |
| 6,969,521 B1 | 11/2005 | Gonzalez et al. |
| 6,994,863 B2 | 2/2006 | Eini et al. |
| 7,014,844 B2 | 3/2006 | Mahalingam et al. |
| 7,029,659 B2 | 4/2006 | Abram et al. |
| 7,060,253 B1 * | 6/2006 | Mundschenk .................. 424/45 |
| 7,078,058 B2 | 7/2006 | Jones et al. |
| 7,137,536 B2 | 11/2006 | Walters et al. |
| 7,225,518 B2 | 6/2007 | Eidenschink et al. |
| 7,235,251 B2 | 6/2007 | Hamer et al. |
| 7,270,828 B2 | 9/2007 | Masuda et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 2001/0006654 A1 | 7/2001 | Cannell et al. |
| 2001/0027218 A1 | 10/2001 | Stern et al. |
| 2001/0036450 A1 | 11/2001 | Verite et al. |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0032171 A1 | 3/2002 | Chen et al. |
| 2002/0035046 A1 | 3/2002 | Lukenbach et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0143188 A1 | 10/2002 | Garvey et al. |
| 2002/0165170 A1 | 11/2002 | Wilson et al. |
| 2002/0182162 A1 | 12/2002 | Shahinpoor et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0031693 A1 | 2/2003 | Breton et al. |
| 2003/0053961 A1 | 3/2003 | Eccard |
| 2003/0078172 A1 | 4/2003 | Guiramand et al. |
| 2003/0114520 A1 | 6/2003 | Pereira et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0206955 A1 | 11/2003 | Sonneville-Aubrun et al. |
| 2003/0215472 A1 | 11/2003 | Bonda et al. |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0078896 A1 | 4/2004 | Hellyer et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0197276 A1 | 10/2004 | Takase et al. |
| 2004/0197295 A1 | 10/2004 | Riedel et al. |
| 2004/0219122 A1 | 11/2004 | Masuda et al. |
| 2004/0219176 A1 | 11/2004 | Dominguez |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0265240 A1 | 12/2004 | Tamarkin et al. |
| 2005/0013853 A1 | 1/2005 | Gil-Ad et al. |
| 2005/0031547 A1 | 2/2005 | Tamarkin et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0101936 A1 | 5/2005 | Gonzales et al. |
| 2005/0106197 A1 | 5/2005 | Blin et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0255048 A1 | 11/2005 | Hirsh et al. |
| 2005/0266035 A1 | 12/2005 | Healy et al. |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |

| | | |
|---|---|---|
| 2006/0014990 A1 | 1/2006 | Kuechler et al. |
| 2006/0018937 A1 | 1/2006 | Friedman |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0057168 A1 | 3/2006 | Larm |
| 2006/0088561 A1 | 4/2006 | Eini et al. |
| 2006/0110418 A1 | 5/2006 | Johnson |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0175799 A1 | 7/2009 | Tamarkin et al. |
| 2009/0180970 A1 | 7/2009 | Tamarkin et al. |
| 2009/0317338 A1 | 12/2009 | Tamarkin et al. |
| 2010/0221194 A1 | 9/2010 | Loupenok |
| 2011/0002969 A1 | 1/2011 | Serraima et al. |

FOREIGN PATENT DOCUMENTS

| | | |
|---|---|---|
| DE | 1926796 | 11/1965 |
| DE | 4140474 | 6/1993 |
| DE | 10138495 | 2/2003 |
| DE | 102004016710 | 10/2005 |
| EP | 0156507 A1 | 10/1985 |
| EP | 0186453 | 7/1986 |
| EP | 211550 | 2/1987 |
| EP | 0214865 A2 | 3/1987 |
| EP | 0216856 | 4/1987 |
| EP | 270 316 | 6/1988 |
| EP | 0270316 | 6/1988 |
| EP | 297436 A2 | 1/1989 |
| EP | 326196 | 8/1989 |
| EP | 336812 | 10/1989 |
| EP | 0391124 A2 | 10/1990 |
| EP | 0404376 | 12/1990 |
| EP | 414920 | 3/1991 |
| EP | 0484530 A1 | 5/1992 |
| EP | 485299 | 5/1992 |
| EP | 0488089 A1 | 6/1992 |
| EP | 504301 | 9/1992 |
| EP | 0506197 A1 | 9/1992 |
| EP | 0 535 327 | 4/1993 |
| EP | 0535327 | 4/1993 |
| EP | 0569773 A2 | 11/1993 |
| EP | 0598412 | 11/1993 |
| EP | 0738516 | 10/1996 |
| EP | 0824911 | 2/1998 |
| EP | 829259 | 3/1998 |
| EP | 676198 | 10/1998 |
| EP | 928608 | 7/1999 |
| EP | 0979654 A1 | 2/2000 |
| EP | 0993827 A1 | 4/2000 |
| EP | 1025836 A1 | 8/2000 |
| EP | 1055425 A2 | 11/2000 |
| EP | 1215258 | 6/2002 |
| EP | 1 287 813 | 3/2003 |
| EP | 1308169 | 5/2003 |
| EP | 1 428 521 | 6/2004 |
| EP | 1438946 | 7/2004 |
| EP | 1189579 | 9/2004 |
| EP | 1475381 | 11/2004 |
| EP | 1483001 | 12/2004 |
| EP | 1500385 | 1/2005 |
| EP | 1600185 | 11/2005 |
| EP | 1734927 | 12/2006 |
| EP | 1758547 | 3/2007 |
| EP | 1584324 | 11/2007 |
| EP | 1889609 | 2/2008 |
| FR | 2736824 | 1/1997 |
| FR | 2774595 A | 8/1999 |
| FR | 2840903 | 12/2003 |
| FR | 2860976 | 4/2005 |
| FR | 2915891 | 11/2008 |
| GB | 808104 | 1/1959 |
| GB | 808105 | 1/1959 |
| GB | 922930 | 4/1963 |
| GB | 933486 A | 8/1963 |
| GB | 1026831 | 4/1966 |
| GB | 1033299 | 6/1966 |
| GB | 1081949 A | 9/1967 |
| GB | 1121358 | 7/1968 |
| GB | 1170152 A | 11/1969 |
| GB | 1347950 | 2/1974 |
| GB | 1376649 | 12/1974 |
| GB | 1397285 | 6/1975 |
| GB | 1408036 | 10/1975 |
| GB | 1489672 A | 10/1977 |
| GB | 2004746 A | 4/1979 |
| GB | 1561423 | 2/1980 |

| | | | | | | |
|---|---|---|---|---|---|---|
| GB | 2114580 | 8/1983 | | WO | WO-99/08649 | 2/1999 |
| GB | 2153686 | 8/1985 | | WO | WO-99/20250 | 4/1999 |
| GB | 2172298 | 9/1986 | | WO | WO-99/37282 | 7/1999 |
| GB | 2166651 | 5/1996 | | WO | WO-9953923 | 10/1999 |
| GB | 2337461 | 11/1999 | | WO | WO-9953923 A1 | 10/1999 |
| GB | 2406791 | 4/2005 | | WO | WO-00/09082 | 2/2000 |
| IL | 0152486 A0 | 5/2003 | | WO | WO 00/15193 | 3/2000 |
| JP | 60001113 | 4/1978 | | WO | WO-0023051 | 4/2000 |
| JP | 55069682 | 5/1980 | | WO | WO-0033825 | 6/2000 |
| JP | 63119420 | 5/1988 | | WO | WO-0038731 | 7/2000 |
| JP | 01100111 | 4/1989 | | WO | WO-00/61076 | 10/2000 |
| JP | 01156906 | 6/1989 | | WO | WO-00/76461 | 12/2000 |
| JP | 02184614 A | 7/1990 | | WO | WO-01/08681 | 2/2001 |
| JP | 2255890 | 10/1990 | | WO | WO-0110961 A1 | 2/2001 |
| JP | 04282311 | 10/1992 | | WO | WO-01/54679 | 8/2001 |
| JP | 4312521 | 11/1992 | | WO | WO-0162209 A2 | 8/2001 |
| JP | 5070340 | 3/1993 | | WO | WO 01/70242 A2 | 9/2001 |
| JP | 5213734 | 8/1993 | | WO | WO 01/70242 A3 | 9/2001 |
| JP | 6100414 | 4/1994 | | WO | WO-01/82880 | 11/2001 |
| JP | 6329532 | 11/1994 | | WO | WO-0185102 A2 | 11/2001 |
| JP | 7215835 | 8/1995 | | WO | WO-0185128 | 11/2001 |
| JP | 2008040899 | 2/1996 | | WO | WO-0195728 | 12/2001 |
| JP | 8119831 | 5/1996 | | WO | WO-02/00820 | 1/2002 |
| JP | 8165218 | 6/1996 | | WO | WO-0215860 | 2/2002 |
| JP | 8277209 | 10/1996 | | WO | WO-0215873 | 2/2002 |
| JP | 9099553 | 4/1997 | | WO | WO-02/28435 | 4/2002 |
| JP | 9110636 | 4/1997 | | WO | WO-02/41847 A1 | 5/2002 |
| JP | 10114619 | 5/1998 | | WO | WO-02/43490 | 6/2002 |
| JP | 3050289 | 9/1998 | | WO | WO-02/062324 | 8/2002 |
| JP | 11250543 | 9/1999 | | WO | WO-02078667 A1 | 10/2002 |
| JP | 2000017174 A | 1/2000 | | WO | WO-02087519 | 11/2002 |
| JP | 2000080017 | 3/2000 | | WO | WO-03000223 A1 | 1/2003 |
| JP | 2000128734 | 5/2000 | | WO | WO-03002082 | 1/2003 |
| JP | 2000191429 | 7/2000 | | WO | WO 03/051294 | 6/2003 |
| JP | 2000239140 | 9/2000 | | WO | WO-03/053292 | 7/2003 |
| JP | 2000351726 | 12/2000 | | WO | WO-03/055445 | 7/2003 |
| JP | 2000354623 | 12/2000 | | WO | WO-03055454 | 7/2003 |
| JP | 2001002526 | 1/2001 | | WO | WO-03/075851 | 9/2003 |
| JP | 2001019606 | 1/2001 | | WO | WO-03092641 A1 | 11/2003 |
| JP | 2001072963 | 3/2001 | | WO | WO-2004017962 | 3/2004 |
| JP | 2002012513 | 1/2002 | | WO | WO-2004037197 | 5/2004 |
| JP | 2002047136 | 2/2002 | | WO | WO-2004037225 A2 | 5/2004 |
| JP | 2002302419 | 10/2002 | | WO | WO-2004/064833 A1 | 8/2004 |
| JP | 2003055146 | 2/2003 | | WO | WO-2004/071479 A1 | 8/2004 |
| JP | 2004047136 A | 2/2004 | | WO | WO-2004064769 | 8/2004 |
| JP | 2004250435 | 9/2004 | | WO | WO-2004078158 | 9/2004 |
| JP | 2005314323 | 11/2005 | | WO | WO-2004078896 A1 | 9/2004 |
| JP | 2005350378 | 12/2005 | | WO | WO-2004093895 | 11/2004 |
| JP | 2006008574 | 1/2006 | | WO | WO 2004/112780 A1 | 12/2004 |
| JP | 2007131539 | 5/2007 | | WO | WO-2005/011567 A2 | 2/2005 |
| KR | 143232 | 7/1998 | | WO | WO-2005/018530 A2 | 3/2005 |
| KR | 2001003063 | 1/2001 | | WO | WO2005/044219 | 5/2005 |
| UA | 66796 | 6/2004 | | WO | WO-2005063224 | 7/2005 |
| WO | WO-8201821 | 6/1982 | | WO | WO-2005/065652 A1 | 7/2005 |
| WO | WO-86/05389 | 9/1986 | | WO | WO-2005/076697 | 8/2005 |
| WO | WO-88/01863 | 3/1988 | | WO | WO-2005/097068 A1 | 10/2005 |
| WO | WO-8801502 | 3/1988 | | WO | WO2005/032522 | 11/2005 |
| WO | WO-88/08316 | 11/1988 | | WO | WO-2005102282 A1 | 11/2005 |
| WO | WO-89/06537 | 7/1989 | | WO | WO-2005102539 | 11/2005 |
| WO | WO90/05774 | 5/1990 | | WO | WO-2005117813 A1 | 12/2005 |
| WO | WO 91/11991 | 8/1991 | | WO | WO-2006/003481 A2 | 1/2006 |
| WO | WO-92/00077 | 1/1992 | | WO | WO-2006/010589 | 2/2006 |
| WO | WO-9205142 A1 | 4/1992 | | WO | WO-2006011046 | 2/2006 |
| WO | WO-92/11839 | 7/1992 | | WO | WO-2006020682 A1 | 2/2006 |
| WO | WO-9325189 | 12/1993 | | WO | WO-2006028339 A1 | 3/2006 |
| WO | WO-9406440 | 3/1994 | | WO | WO-2006031271 A2 | 3/2006 |
| WO | WO-96/03115 | 2/1996 | | WO | WO-2006045170 | 5/2006 |
| WO | WO 96/19921 | 4/1996 | | WO | WO-2006079632 A1 | 8/2006 |
| WO | WO-9624325 A1 | 8/1996 | | WO | WO-2006081327 | 8/2006 |
| WO | WO 96/27376 | 9/1996 | | WO | WO-2006091229 A2 | 8/2006 |
| WO | WO-96/39119 | 12/1996 | | WO | WO-2006100485 A1 | 9/2006 |
| WO | WO-9703638 | 2/1997 | | WO | WO-2006120682 | 11/2006 |
| WO | WO-97/39745 | 10/1997 | | WO | WO-2006121610 A2 | 11/2006 |
| WO | WO-9817282 | 4/1998 | | WO | WO-2006122158 | 11/2006 |
| WO | WO-98/18472 | 5/1998 | | WO | WO-2006/129161 | 12/2006 |
| WO | WO-98/19654 | 5/1998 | | WO | WO-2006/131784 | 12/2006 |
| WO | WO-98/21955 | 5/1998 | | WO | WO-2007/007208 | 1/2007 |
| WO | WO-98/23291 | 6/1998 | | WO | WO-2007/012977 | 2/2007 |
| WO | WO-98/36733 | 8/1998 | | WO | WO-2007/023396 | 3/2007 |

| | | |
|---|---|---|
| WO | WO-2007031621 A2 | 3/2007 |
| WO | WO2007/050543 | 5/2007 |
| WO | WO-2007/054818 | 5/2007 |
| WO | WO-2007/072216 | 6/2007 |
| WO | WO-2007/085899 | 8/2007 |
| WO | WO-2007085902 A2 | 8/2007 |
| WO | WO-2007/099396 | 9/2007 |
| WO | WO-2007111962 A2 | 10/2007 |
| WO | WO-2007/039825 | 11/2007 |
| WO | WO2008/008397 | 1/2008 |
| WO | WO-2008010963 | 1/2008 |
| WO | WO-2008/038147 | 4/2008 |
| WO | WO-2008/075207 | 6/2008 |
| WO | WO-2008075207 A2 | 6/2008 |
| WO | WO-2008087148 A2 | 7/2008 |
| WO | WO-2008110872 A2 | 9/2008 |
| WO | WO-2009007785 A2 | 1/2009 |
| WO | WO-2009069006 A2 | 6/2009 |
| WO | WO-2009072007 A2 | 6/2009 |
| WO | WO-2009087578 A2 | 7/2009 |
| WO | WO-2009090495 A2 | 7/2009 |
| WO | WO-2009090558 A2 | 7/2009 |
| WO | WO-2009098595 A2 | 8/2009 |
| WO | WO-2011039637 | 4/2011 |
| WO | WO-2011039638 | 4/2011 |

OTHER PUBLICATIONS

Raymond, Iodine as an Aerial Disinfectant, Journal of Hygeine, vol. 44 No. 5, pp. 359-361, 1946.*
Kumar et al., Appication of broad spectrum antiseptic povidone iodine as powerful action: review, Journal of Pharmaceutical Science and technology, vol. 1, No. 2, pp. 48-58, 2009.*
Schutze, Ionie and sodium hypochlorite as wound disinfectants, The British Medical Journal, pp. 921-922, 1915.*
Karusa et al., Treatment of Patients with Major Depressive Disorder, Second Edition, pp. 1-78, 2000.*
Kleber et al., Treatment of Patients with Substance abuse disorders, Second Edition, pp. 1-276, 2006.*
Heart Failure, The Merck Manual, 2008 <<http://www.merck.com/mmhe/sec03/ch025/ch025a.html>>.*
Prevent. (2007). In the American Heritage® Dictionary of the English Language. Retrieved from http://www.credoreference.com/entry/hmdictenglang/prevent.*
International Search Report, International Patent Application No. PCT/IB2007/003759, Foamix Ltd., Jul. 8, 2008 (2 pages).
D.W.A. Sharp Dictionary of Chemistry, Penguin Books, 1983, 3 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Material Safety Data Sheet, Progesterone, Apr. 26, 2006, 5 pages.
"Licking Vaginal Dryness Without a Prescription," Estronaut, Dec. 14, 2008, 3 pages.
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Gill, A.M, et al., "Adverse Drug Reactions in a Paediatric Intensitve Care Unit," Acta Paediatr 84:438-441, 1995.
Gschnait, F., et al., "Topical Indomethacin Protects from UVB and UVA Irradiation," Arch. Dermatol. Res. 276:131-132, 1984.
Hall, Karla, "Diaper Area Hemangiomas: A Unique Set of Concerns," http://members.tripod.com/~Michelle_G/diaper.html, Dec. 1, 2008, 8 pages.
Skin Biology, CP Serum—Copper-Peptide Serum for Skin Regeneration and Reducing Wrinkles, Skin Biology, http;//web.archive.org/web/20030810230608/http://www.skinbio.com/cpserum.html, Dec. 1, 2008, 21 pages.
Galligan, John et al., "Adhesive Polyurethane Liners for Anterior Restorations," J. Dent. Res., Jul.-Aug. 1968, pp. 629-632.
Innocenzi, Daniele et al., "An Open-Label Tolerability and Effiacy Study of an Aluminum Sesquichlorhydrate Topical Foam in Axilliary and Palmar Primary Hyperhidrosis," Dermatologic Therapy, vol. 21, S27-S30, 2008.

Coetzee, Nicol et al., "Acceptability and Feasibility of Micralax Applicators and of methyl Cellulose Gel Placebo for Large-Scale Clinical Trials of Vaginal Microbicides," Concise Communication, 2001, vol. 15, No. 14, pp. 1837-1842.
Pendergrass, P.B. et al., "The Shape and Dimension of the Human Vagina as Seen in Three-Dimensional Vinyl Polysiloxane Casts," Gynecol Obstet. Invest. 1996;42(3), 2 pages.
Merriam-Webster Online Dictionary, 2008, "Mousse," Merriam-Webster Online, Dec. 8, 2008 http://www.merriam-webster.com/dictionary/mousse.
Abstract for TR-436-t-Butyl Alcohol, National Toxicology Program, Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Denatonium Benzoate, Chemical Structure Molecular Form Reference Standard, http://www.newdruginfo.com/pharmaceopeia/usp28/v28230/usp28nf23s0_m22790.htm Accessed Dec. 9, 2008, 2 pages.
Scott, Roy R., as Published in Pharmaceutical Dosage Forms; Disperse Systems, vol. 3, Copyright 1998, 120 pages.
Flick, Cosmetic and Toiletry Formulations, vol. 5, 2nd Edition, Copyright 1996, (259-309), 63 pages.
Arisan, 8 pages, http://www.arisankimya.com/kozmetik.htm Accessed Dec. 10, 2008.
Kinnuen, T., et al., "Skin Reactions to Hexylene Glycol," Contact Dermatitis, Sep. 21, 1989, 2 pages.
Sigma-Aldrich, Ethanol, E7023 Ethanol 200 Proof (Absolute) for Molecular Biology, 2 pages http://www.sigmaaldrich.com/catalog/ProductDetail.do?N4=E7023SIAL&N5=SEARCH_CONCAT_PNOBRAND_KEY&F=SPEC Accessed Dec. 9, 2008.
Material Safety Data Sheet, Alcohol SDA 40B.http://www.pharmcoprod.com/pages/MSDS/SDA_40B_200.pdf Pharmco-AAPER, Dec. 2005, 2 pages Accessed Dec. 9, 2008.
Barry, B.W. et al, Comparative bio-availability and activity of proprietary topical corticosteroid preparations: vasoconstrictor assays on thirty-one ointments, British Journal of Dermatology, 93, 563-571, 1975.
Tamarkin, D., et al. Body Cavity Foam, U.S. Appl. No. 11/116,761, filed Apr. 28, 2005.
Tamarkin, D., et al. Moisturizing Foam Containing Lanolin, U.S. Appl. No. 11/099,942, filed Apr. 6, 2005.
Tamarkin, D., et al. Nonsteroidal Immunomodulating Kit and Composition and Uses Thereof, U.S. Appl. No. 11/078,902, filed Mar. 11, 2005.
Tamarkin, D., et al. Steroid Kit and Foamable Composition and Uses, U.S. Appl. No. 11/114,410, filed Apr. 26, 2005.
Tamarkin, D., et al. Vasoactive Kit and Composition and Uses Thereof, U.S. Appl. No. 11/124,676, filed May 9, 2005.
Martindale, The extra pharmacopoeia [28th] edition, Eds.: Reynolds, J.E.F. and Prasad, A.B., The Pharmaceutical Press, London, 1982, pp. 862-864.
Wormser et al. *Letters to the Editor*, Burns, 1998, 24, 383.
Wormser et al. Arch. Toxicol., 1997, 71, 165-170.
"HLB Systems", http://pharmcal.tripod.com/ch17.htm, Accessed Sep. 17, 2010, pp. 1-3.
Adachi, Shuji. "Storage and Oxidative Stability of O/W/ Nano-emulsions." Foods Food Ingredients. J. Jpn. vol. 209, No. 11. 2004. 1 page.
Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400- Hydrogen Peroxide Pastes Used to Treat Infected Wounds,"Antimicrobial Agents and Chemotherapy, vol. 35, No. 9, pp. 1799-1803, 1991.
Anton, N. et al. "Water-in-Oil Nano-Emulsion Formation by the phase inversion Temperature Method: A Novel and General Concept, a New Template for Nanoencapsulation." University of Angers. Paris, France. No Date Listed. 2 pages.
Arct, et al., "Common Cosmetic Hydrophilic Ingredients as Penetration Modifiers of Flavonoids", International Journal of Cosmetic Science, 24(6):357-366 (2002) - Abstract, 1 page.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.

Austria, et al., "Stability of Vitamin C Derivatives in Solution and Topical Formulations", Journal of Pharmaceutical and Biomedical Analysis, 15:795-801 (1997).

Benet, et al., App-lication of NMR for the Determination of HLB Values of Nonionic Surfactants, Journal of the American Oil Chemists Society, vol. 49, 1972, 499-500.

Berstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfacants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstrace, 1 page.

Bronopol. Revtrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carbowax 1000MSDS; http://www.sciencelab.com/xMSDS-Polyethylene.sub.--glycol.sub.--1000-9926-622. Accessed Dec. 13, 2008, 6 pages.

Carelli, et al., "Effect of Vehicles on Yohimbine Permeation Across Excised Hairless Mouse Skin", Pharm Acta Hely, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Cheshire, et al., Disorders of Sweating, www.medscape.com, Semin Neurol 23(4):399-406, 2003.

Chevrant-Breton, et al., "Etude du Traitement Capillaire <<Bioscalin>> dans les Alopecies Diffuses de la Femme", Gazette Medicale, 93(17):75-79 (1986).

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (Nov.), p. S475 (1997), 2 pages.

Colloidal Silica. Retrieved online on Jun. 4, 2011. <URL:http://www.grace.com/engineeredmaterials/materialsciences/colloidalsilica/default.aspx>. Copyright 2011. 4 pages.

Croda 2. Croda Cetomacrogol 1000 Product Information Sheet. 2011 (no month given). 1 page.

Croda. Aracel 165 Product Summary. 2011 (no month given). 1 page.

Dalby, "Determination of Drug Solubility in Aerosol Propellants," Pharmaceutical Research, vol. 8, No. 9, 1991, pp. 1206-1209.

Dawber, et al., "Hypertrichosis in Females Applying Minoxidil Topical Solution and in Normal Controls", JEADV, 17:271-275 (2003).

Dentinger, et al., "Stability of Nifedipine in an Extemporaneously Compounded Oral Solution", American Journal of Health-System Pharmacy, 60(10):1019-1022 (2003)—Abstract, 1 page.

Draelos, Z. D. "Antiperspirants and the Hyperhidrosis Patients." Dermatologic Therapy. 2001. vol. 14. pp. 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edirisinghe, et al., "Effect of fatty acids on endothelium-dependent relaxation in the rabbit aorta", Clin Sci (Lond). Aug. 2006; 111(2): 145-51.

Edwards, "Imiquimod in Clinical Practice", J. Am Acad Dermatol., 43(1, Pt 2):512-517 (2000)—Abstract, 1 page.

Emulsifiers with HLB values. http://www.theherbarie.com/files/resources-center/formulating/Emulsifiers-.sub.--HLB.sub.--Values. pdf accessed Aug. 5, 2009 (3 pps).

Encyclopedia of Pharmaceutical Technology, Second Edition, vol. 3, Copyright 2002, 4 pages.

English machine translation of JP-08165218 (1996), 9 pages.

English translation of abstract for Japanese Patent Publication No. 4892282 (1992), 1 page.

Esposito, E. et al. "Nanosystems for Skin Hydration: A Comparative Study." International Journal of Cosmetic Science. 29. 2007. pp. 39-47.

Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.

European Official Action, European Patent Application No. 06831721.3, Feb. 3, 2009, 9 pages.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Fonatana, Anthony J., "Water Activity: Why It is Important for Food Safety," International Conference on Food Safety, Nov. 16-18, 1998, pp. 177-185.

Gallarate, et al., "On the Stability of Ascorbic Acid in Emulsified Systems for Topical and Cosmetic Use", International Journal of Pharmaceutics, 188:233-241 (1999).

Gelbard et al. "Primary Pediatric Hyperhidrosis: A Review of Current Treatment Options." Pediatric Dermatology. 2008. 25 (6). pp. 591-598.

Gladkikh, "Ascorbic Acid and Methods of Increasing its Stability in Drugs", Translated from Khimiko-Farmatsevticheskii Zhurnal, 4(12):37-42 (1970)—1 page.

Glaser, et al., Hyperhidrosis: A Comprehensive and Practical Approach to Patient Management, Expert Rev. Dermatol. 1(6), 773-775 (2006).

Graves, S. et al. "Structure of Concentrated Nanoemulsions." The Journal of Chemical Physics.. 122 America Institute of Physics. Published Apr. 1, 2005. 6 pages.

Groveman, et al., "Lack of Efficacy of Polysorbate 60 in the Treatment of Male Pattern Baldness", Arch Intern Med, 145:1454-1458 (1985).

Hakan, et al., "The protective effect of fish oil enema in acetic acid and ethanol induced colitis," The Turkish Journal of Gasroenterology, 2000, vol. 11, No. 2, pp. 155-161.

Hallstar. Retrieved online on Jun. 4, 2011. <URL:http://www.hallstar.com/pis.php?product=1H022>. 1 page.

Harrison, et al., "Effects of cytokines and R-837, a cytokine inducer, on UV-irradiation augmented recurrent genital herpes in guinea pigs", Antivial Res., 15(4):315-322 (1991).

Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Hashim, et al. "Tinea versicolor and visceral leishmaniasis," Int J Dermatol., Apr. 1994; 33(4), pp. 258-259 (abstract only). 2 pages.

Hepburn, Nc., "Cutaneous leishmaniasis," Clin Exp Dermatol, Jul. 2000; 25(5), pp. 363-370 (abstract only). 2 pages.

Hill, Randall M. (Ed.) Silicone Surfactants, Table of Contents and Chapter 7, "Silicone Surfactants: Applicants in the Personal Care Industry," by David T. Floyd, 1999 (30 pages).

http://ibabydoc.com/online/diseaseeczema.asp., Atopic Dermatitis, Copyright 2000, 6 pages.

http://web.archive.org/web/20000106225413/http://pharmacy.wilkes.edu/kibbeweb/lab7.html, Characteristics of Surfactants and Emulsions, Jan. 29, 2010, 5 pages.

http://www.agworkshop.com/p3.asp, AG&Co. Essential oil workshop. 1 page. Accessed Jan. 31, 2010.

Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.

ICI Americas Inc. "The HLB System: A Time-Saving Guide to Emulsifier Selection." Mar. 1980. pp. 1-22.

Ikuta, et al., "Scanning Electron Microscopic Observation of Oil/Wax/Water/Surfacant System", Journal of SCCJ, 34(4):280-291 (2004)—Abstract, 1 page.

Indomethacin. Retrieved online on Jun. 3, 2011. <URL:http://it03.net/com/oxymatrine/down/1249534834.pdf>. Aug. 15, 2009. 3 pages.

International Search Report and Written Opinion for International Application No. PCT/IB10/02241 mailed Feb. 10, 2011. 9 pages.

International Search Report and Written Opinion for International Application No. PCT/IB10/02613 mailed Mar. 16, 2011.9 pages.

International Search Report and Written Opinion for International Application No. PCT/IB10/02617 mailed Mar. 15, 2011. 10 pages.

International Search Report and Written Opinion, International Application No. PCT/IB2006/003628, Foamix Ltd., Dec. 7, 2007, 15 pages.

International Search Report and Written Opinion, International Application No. PCT/US2007/004459, Foamix Ltd., Dec. 9, 2008, 15 pages.

International Search Report and Written Opinion, International Patent Application No. PCT/IB2006/004026, Foamix, Ltd., Jun. 20, 17 pages.

International Search Report for International Application No. PCT/IB2006/003974, Feb. 25, 2008 (3 pages).

International Search Report from PCT/IB2006/003519, Mailed Dec. 3, 2007. 1 page.

International Search Report, International Patent Application No. PCT/IB2007/003463, Foamix, Ltd., Jul. 18, 2008, 3 pages.

International Search Report, International Patent Application No. PCT/IB2007/003759, Foamix Ltd., Jul. 8, 2008 (3 pages).

Invitation to Pay Additional Fees for International Application No. PCT/IB2009/005012 mailed Jul. 27, 2010. 13 pages.

Izquierdo, P. et al. "Formation and Stability of Nano-Emulsions Prepared Using the Phase Inversion Temperature Method." University of Barcelona. Sep. 17, 2001. 1 page.

Kalkan, et al., The Measurement of Sweat Intensity Using a New Technique, Tr. J. of Medical Sciences 28, 515-517 (1998).

Kanamoto, et al., "Pharmacokinetics of two rectal dosage forms of ketoprofen in patients after anal surgery," J Pharmacobiodyn., Mar. 1988; 11(3):141-5.

Kang,et al., "Enhancement of the Stability and Skin Penetration of Vitamin C by Polyphenol", Immune Netw., 4(4):250-254 (2004)—Abstract, 1 page.

Kathon.TM. CG (product information sheet by Rohm and Haas, Jun. 2006). 9 pages.

Kim, "Stability of Minoxidil in Aqueous Solution", Yakhak Hoechi, 30(5):228-231 (1986)—Abstract, 1 page.

Koerber, S., "Humectants and Water Activity," Water Activity News, 2000, ISSN No. 1083-3943. 8 pages.

Kreuter, J. "Nanoparticles and microparticles for drug and vaccine delivery," J. Anat. (1996) 189, pp. 503-505.

Kwak et al. "Study of Complete Transparent Nano-Emulsions which Contain Oils." IFSCC Conference 2003, Seoul, Korea, Sep. 22-24, 2003. 3 pages.

Lautenschlager, Dr. Hans. "A Closer Look on Natural Agents: Facts and Future Aspects." Kosmetic Konzept. Kosmetische Praxis. 2006 (no month given). (5), 8-10. 3 pages.

Lebwohl et al. "Treatment of Psoriasis. Part 1. Topical Therapy and Phototherapy." J. Am. Acad. Dermatol. 45:487-498. Oct. 2001.

Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).

Leung, et al., "Bioadhesive Drug Delivery in Water-Soluble Polymers," American Chemical Society, Chapter 23, 1991, pp. 350-366.

Li, et al., "Solubility Behavior of Imiquimod in Alkanoic Acids", Abstract 3029, Pharmaceutical Research, vol. 14, No. 11 Supplemental (Nov.), p. S475 (1997), 2 pages.

Lippacher, A. et al. "Liquid and Semisolid SLN Dispersions for Topical Application" Rheological Characterization. European Journal of Pharmaceutics and Biopharmaceutics. 58. 2004. pp. 561-567.

Lupo, "Antioxidants and Vitamins in Cosmetics", Clinics in Dermatology, 19:467-473 (2001).

Material Safety Data Sheet, Science Lab.com, Polyethylene Glycol 1000, MSDS, Nov. 6, 2008, 6 pages.

Merck Index, An Encyclopedia of Chemicals, Drugs, and Biologicals. 13$^{th}$ Edition. O'Neil et al eds. Entries 1058, 2350, 6143, and 8803. 2001. 7 pages.

Merck Manual Home Edition. "Excessive Sweating: Sweating Disorders." Accessed Apr. 14, 2011 at www.merckmanuals.com/home/print/sec18/ch206/ch206c.html. 2 pages.

Merriam Webster Online Dictionary [online] retrieved from http://www.merriam-webster.com/cgi-bin/dictionary?book=dictionary&va=derivative on Jul. 5, 2008; 1 page.

Messenger, et al., "Minoxidil: Mechanisms of Action on Hair Growth", British Journal of Dermatology, 150:186-194 (2004).

Metronidazole. www.usp.org/pdf/EN/veterinary/metronidazole.pdf. accessed Sep. 10, 2009, 4 pages.

Metz, et al., "A Phase I Study of Topical Tempol for the Prevention of Alopecia Induced by Whole Brain Radiotherapy", Clinical Cancer Research, 10:6411-6417 (2004).

Meucci, et al., "Ascorbic Acid Stability in Aqueous Solutions", Acta Vitaminol Enzymol, 7(3- 4):147-153 (1985)—Abstract, 1 page.

MMP Inc. International Development and Manufacturing, "Formulating specialities," http://mmpinc.com, 3 pages. Feb. 2, 2010.

Molan, Peter Clark, "World Wide Wounds," Dec. 2001, 13 pages.

No Author Listed. "Opitmization of Nano-Emulsions Production by Microfluidization." European Food Research and Technology. vol. 225, No. 5-6. Sep. 2007. Abstract. 1 page.

Office Action for U.S. Appl. No. 11/430,437, Tamarkin et al., May 9, 2008, 27 pages.

Office Action received from the U.S. Patent Office, U.S. Appl. No. 11/430,599, Jul. 28, 2008 (59 pages).

Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).

OM Cinnamate. http://www.makingcosmetics.com/sunscreens/OM-Cinnamate-p102.html accessed Sep. 26, 2009, 1 page.

Pakpayat, et al., "Formulation of Ascorbic Acid Microemulstions with Alkyl Polyglycosides", European Journal of Pharmaceutics and Biopharmaceutics, 72:444-452 (2009).

Paula. http://ww.cosmeticscop.com/cosmetic-ingredient-dictionary/definition/259/c12-15-alkyl-benzoate.aspx. Printed Oct. 24, 2010. 1 page.

PCT Search Report and Written Opinion for International Application No. PCT/IB2010/001126 mailed Apr. 20, 2011, 12 pages.

Prescription Information for Aldara, Mar. 2007 (29 pages).

Psoriasis, http://www.quickcare.org/skin/causes-of0psoriasis.html. Accessed Sep. 9, 2010 - 3 pages.

Purcell, Hal C. "Natural Jojoba Oil Versus Dryness and Free Radicals." Cosmetics and Toiletries Manufacture Worldwide. 1988. 4 pages.

Raschke, et al., "Topical Activity of Ascorbic Acid: From In Vitro Optimization to In Vivo Efficacy", Skin Pharmacology and Physiology, 17(4):200-206 (2004)—Abstract, 1 page.

Receptacle. Merriam Webster. Http://www.merriam-webster.com/dictionary/receptacle. Accessed Jul. 12, 2011. 1 page.

Richwald, "Imiquimod", Drugs Today, 35(7):497 (1999)—Abstract, 1 page.

Rieger and Rhein. "Emulsifier Selection/HLB." Surfactants in Cosmetics. 1997 (no month given). 1 page.

Rosacea, http://clinuvel.com/skin-conditions/common-skin-conditions/rosacea#h0-6-prevention. Accessed Sep. 9, 2010, 5 pages.

Savin, et al., "Tinea versicolor treated with terbinafine 1% solution," Int J. Dermatol, Nov. 1999; 38(11), pp. 863-865.

Schmidt A., "Malassezia furfur: a fungus belonging to the physiological skin flora and its relevance in skin disorders," Curtis., Jan. 1997; 59(1), pp. 21-4 (abstract).

Scientific Discussion for the approval of Aldara, EMEA 2005 (10 pages).

Seborrheic Dermatitis, http://www.cumc.columbia.edu/student/health/pdf/R-S/Seborrhea%20Dermatitis.pdf. Access Sep. 9, 2010, 2 pages.

Shear, et al., "Pharmacoeconomic analysis of topical treatments for tinea infections," Pharmacoeconomics. Mar. 1995; 7(3); pp. 251-267 (abstract only). 2 pages.

Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.

Shim, et al., "Transdermal Delivery of Mixnoxidil with Block Copolymer Nanoparticles", J. Control Release, 97(3):477-484 (2004)—Abstract, 1 page.

Sigma Aldrich, "HLB-Numbers In Lithography Nanopatterning," http://www.sigmaaldrich.com/materials-science/micro-and-nanoelectronics/I-ithographynanopatterning/hlb-number.html, accessed: Feb. 2, 2009, pp. 1-3.

Sigma-Aldrich, Material Safety Data Sheet, Hydroxyethyl Cellulose, Mar. 3, 2004, 5 pages.

Silicone. Definition. Retrieved Apr. 19, 2011 from http://www.oxforddictionaries.com/definition/silicone?view=uk. 1 page.

Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.

Skin Deep Cosmetics. PPG-40-PEG-60 Lanolin Oil http://www.cosmeticsdatabase.com/ingredient/722972/PPG-40-PEG60_Lanolin_Oil/?ingred06=722972. 3 pages.

Sonneville-Aubrun, O. et al. "Nanoemulsions: A New Vehicle for Skincare Products." Advances in Colloid and Interface Science. 108-109.. 2004. pp. 145-149.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only). 1 page.

Sreenivasa, et al., "Preparation and Evaluation of Minoxidil Gels for Topical Application in Alopecia", Indian Journal of Pharmaceutical Sciences, 68(4):432-436 (2006), 11 pages.

Stehle, et al., "Uptake of Minoxidil from a New Foam Formulation Devoid of Propylene Glycol to Hamster Ear Hair Follicles", Abstract 606, 1 page.

Sugisaka, et al., "The Physiochemical Properties of Imiquimod, The First Imidazoquinoline Immune Response Modifier", Abstract 3030, Pharmaceutical Research, vol. 14, No. 11 Supplemental (Nov.), pg. S475 (1997), 2 pages.

Surfactant. Wikipedia—http://en.wikipedia.org/wiki/surfactant. Printed Oct. 24, 2010. 1 page.

Sweetman, Sean C. Martindale: The Complete Drug Reference. 33rd Edition. London. Pharmaceutical Press. Jun. 21, 2002. pags. 1073 and 1473. 5 pages.

Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.

Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.

Tanhehco, "Potassium Channel Modulators as Anti-Inflammatory Agents", Expert Opinion on Therapeutic Patents, 11(7):1137-1145 (2001)—Abstract, 3 pages.

Tarumoto, et al., Studies on toxicity of hydrocortisone 17-butyrate 21-propionate -1. Acute toxicity of hydrocortisone 17-butyrate 21-propionate and its analogues in mice, rats and dogs (authors trans), J Toxicol Sci., Jul. 1981; 6 Suppl: 1-16.

Tata, et al., "Penetration of Minoxidil from Ethanol Propylene Glycol Solutions: Effect of Application Volume on Occlusion", Journal of Pharmaceutical Sciences, 84(6):688-691 (1995).

Tata, et al., "Relative Influence of Ethanol and Propylene Glycol Cosolvents on Deposition of Minoxidil into the Skin", Journal of Pharmaceutical Sciences, 83(10):1508-1510 (1994).

Torres-Rodriguez, JM., "New topical antifungal drugs," Arch Med Res. 1993 Winter; 24(4), pp. 371-375 (abstract). 2 pages.

Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73DA849-80CA-5FB784E866B576D1. Accessed Dec. 9, 2008, 4 pages.

Trofatter, "imiquimod in clinical Practice", European Journal of Dermatology, 8(7 Supp.):17-19 (1998)—Abstract, 1 page.

Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.

Tsai, et al., "Effect of Minoxidil Concentration on the Deposition of Drug and Vehicle into the Skin", International Journal of Pharmaceutics, 96(1-3):111-117 (1993)—Abstract, 1 page.

Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).

Tyring, "Immune-Response Modifiers: A New Paradigm in the Treatment of Human Papillomavirus", Current Therapeutic Research, 61(9):584-596 (2000)—Abstract, 1 page.

Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.

Veron, et al., "Stability of Minoxidil Topical Formulations", Ciencia Pharmaceutica, 2(6):411- 414 (1992), Abstract, 1 page.

Wermuth, C.G. "Similarity in drugs: reflections on analogue design," Drug Discovery Today, vol. 11, Nos. 7/8, Apr. 2006, pp. 348-354.

Williams, "Scale up of an olive/water cream containing 40% diethylene glycol momoethyl ether", Dev. Ind. Pharm., 26(1):71-77 (2000).

* cited by examiner

FOAMABLE IODINE COMPOSITIONS

RELATED APPLICATIONS

This application is a divisional of and claims the benefit of priority under 35 U.S.C. §120 to U.S. patent application Ser. No. 10/835,359, filed Apr. 28, 2004, entitled "Foamable Iodine Compositions," which claims the benefit of priority under 35 U.S.C. §119(e) to U.S. Provisional Patent Application No. 60/466,094, filed Apr. 28, 2003, entitled "Foamable Iodine Compositions," the entire contents of both of which are incorporated herein by reference.

FIELD OF THE INVENTION

The present invention relates to a foamable composition of matter comprising iodine. The invention further relates to compositions that, when provided in a suitable foaming system, evolve into foam, effective in the topical treatment of various skin conditions.

BACKGROUND OF THE INVENTION

Iodine and iodine complex preparations are widely employed as disinfectants in human and veterinary medicine. Iodine has a powerful bactericidal and fungicidal action and is also active against viruses. It is used as topical antiseptic agents for treatment of small wounds, abrasions and other skin lesions such as herpes simplex. Iodine containing compositions are used for protective treatment of a skin area to be dissected.

Iodine preparations are used in veterinary medicine as post-milking disinfecting treatment of the udders. Iodine is also effectively used for disinfection of drinking water and swimming pool water (Martindale, *The extra pharmacopoeia, [28TH] edition, Eds.: Reynolds, J. E. F. and Prasad, A. B., The Pharmaceutical Press, London,* 1982, pp. 862-864).

Topical iodine preparations possess counter-irritating activity in rheumatism, tenosynovitis and in inflammatory diseases of the peripheral nervous system and muscles. Additional pronounced counter-irritating activity of iodine was demonstrated against skin irritation caused by chemical and thermal stimuli. Iodine is also effective against other skin irritants such as mechlorethamine, divinylsulfone, iodoacetic acid and cantharidine (*Wormser et al. Arch. Toxicol.* (1997) 71, 165-170).

Molecular iodine ($I_2$) is practically water insoluble unless iodide (sodium or potassium salts) is present in the solution to form the water-soluble ion ($I_3^-$). Iodine can be dissolved in ethanol but precipitates in the presence of water. Thus, iodine tincture (which contains ethyl alcohol and water) must also contain iodide to form $I_3^-$ for proper dissolution.

Iodine formulations using other solvents or carriers are known. In some cases, these formulations are shown to have greater iodine solubility or improved iodine release. In some cases, the iodine formulations are demonstrated to be more potent as antiseptics than currently available commercial iodine preparations.

Post-exposure treatment with topical povidone (polyvinylpyrolidone)-iodine preparation has been shown to provide significant protection against mustard gas (sulfur mustard, SM)-induced skin lesions (*Wormser et al. Arch. Toxicol.* (1997) 71, 165-170). Studies also have shown the counter-irritating activity of povidone-iodine against thermal stimuli in humans (*Wormser, Burns* (1998) 24, 383). The experience with patients after accidental heat burns (mostly of grade I; caused by hot water or oil or by hot steam) has shown that topical application of povidone-iodine ointment immediately after the stimulus reduced the degree of skin lesions. The shorter the interval between stimulus and treatment the better the protection achieved.

U.S. Pat. No. 5,071,648 discloses a composition containing acetalized polyvinyl alcohol complexed with iodine, which releases free iodine in the presence of water.

WO 01/70242 discloses a composition including molecular iodine and tetraglycol (TG) that facilitates the dissolution of iodine, enhances its antiseptic effect, and remains stable in the presence of water, in contrast to other iodine solvents, such as ethanol, in which iodine precipitates after water addition. Povidone-iodine complex (PVP-I) may also be dissolved in TG or a TG water system. A pharmaceutically acceptable vehicle according to WO 01/70242 includes an oil/water or a water/oil emulsion, a solution, a suspension, a gel, an ointment, a patch, or an aerosol, preferably solutions, gels and washable ointments.

Despite many years of usage in topical therapy, iodine compositions are still restricted to the conventional list of dosage forms, consisting of water/oil emulsions, solutions, suspensions, gels, ointments, patch, or aerosols. All these preparations comprise liquid or semi-liquid substances, having continuous texture and consistency and possessing specific gravity of 0.7-1.1. Such preparations are disadvantageous, when intended to treat relatively large areas. They are even more disadvantageous when the area to be treated is sensitive, such as area with burns or open wounds, where rubbing a liquid or semi-solid formulation is difficult and painful.

Certain foamable formulations are known in the art.

U.S. Pat. No. 5,716,611 discloses a topical formulation comprising an anti-microbially effective amount of povidone-iodine and from 2% to about 30% of a water-soluble emollient comprising from about 1 to about 99% ethoxylated higher aliphatic alcohol and from about 1 to about 99% ethoxylated cholesterol derivative. The composition includes thickening agents and surfactants that provide foaming upon rubbing on the applied surface.

U.S. Pat. No. 6,258,374 provides a pharmaceutical composition for rectal or vaginal application containing at least two parts wherein the composition comprises (i) two or more physiologically acceptable substances each in separate parts of the composition which are such that on admixture they react to produce a physiologically acceptable gas; (ii) in at least one part of the composition a polymer stabilizer which is adapted to facilitate the formation of a water-soluble collapsible foam structure; and (iii) in at least one part of the composition a pharmaceutically active substance. One of the optional active substances is iodine.

International patent application WO 96/19921 discloses a composition having biocidal activity comprising an active agent selected from iodine or a compound or complex thereof and a polymeric solubilizing agent. The composition may be a foam.

U.S. Pat. No. 6,187,290 teaches physiologically acceptable foam including a foamable carrier separately packaged from an active ingredient. The active ingredient may be, among others, povidone-iodine. Surfactants, humectants and plasticizers may be optionally included.

U.S. Pat. No. 5,951,993 discloses a composition including a lower alcohol and water in a weight ratio of about 35:65 to 100:0, and a thickener system. The thickener system includes at least two emulsifiers, each emulsifier containing at least one hydrophobic group and at least one hydrophilic group. The composition optionally contains iodine or a complexed form of iodine. The composition is useful as a presurgical scrub replacement, a lotion or other hand preparation.

U.S. Pat. No. 5,672,634 describes a rigid, cellular PVP-I foam product, useful as an iodophor, containing about 0.1-2% cross linker and about 16-18% total inorganic iodine.

U.S. Pat. No. 5,545,401 teaches a foaming gel consisting essentially of water, povidone and iodine. In one embodiment water is added to the gel in a closed container pressurized at between 1 and 3 atmospheres with pentane so that when the mixture is returned to atmospheric pressure it spontaneously forms a foam.

U.S. Pat. No. 5,254,334 describes an anhydrous cream composition comprising (a) glycerin in an amount from about 40% to about 60% by weight based on the weight of the total composition; (b) sodium cocoyl isethionate in an amount from about 10 to about 19% by weight based on the weight of the total composition; (c) emollients in an amount from about 10 to about 40% by weight based on the weight of the total composition; and (d) sodium lauryl sulfate in an amount from about 1 to about 5% by weight based on the weight of the total composition. The composition may further comprise a foam booster or active ingredients such as PVP-iodine.

U.S. Pat. No. 4,271,149 discloses a germicidal iodine composition containing an aqueous solution of elemental iodine and at least one organic substance which slowly reacts with iodine selected from the group consisting of iodine complexing polymers, surface active agents, alcohols, polyols and water soluble solvents. The iodine composition is stable for extended storage by providing balanced sources of iodide ion in the range of about 0.025% to 0.5% and iodate ion in the range of about 0.005% to 0.2% while maintaining a pH within the range of pH 5-7. Foam stabilizers are optional components of the composition.

New topical dosage forms are desired to deliver iodine and to treat skin conditions that respond to iodine topical application. A simple-to-use breakable foam, having low specific gravity and being easily spreadable on large skin areas, is particularly desirable.

SUMMARY OF THE INVENTION

The present invention provides a foamable composition including iodine, water, a foam adjuvant, a surface-active agent and a gelling agent that is easily applied and provides high availability of iodine to the applied surface.

According to one aspect the present invention, a foamable composition includes iodine, water, a foam adjuvant, a surface active agent and a gelling agent, in the following concentrations:

about 0.1% to about 5% by weight iodine;
about 80% to about 99.6% by weight of at least one solvent;
about 0.1% to about 5% by weight of at least one foam adjuvant;
about 0.1% to about 5% by weight of at least one surface active agent; and
about 0.1% to about 5% by weight of at least one gelling agent.

The % values presented herein are provided on a weight (w/w) basis of the total composition.

The composition according to one or more embodiments of the present invention, when provided in a suitable foaming device, forms a foam that is effective in the topical treatment of various skin conditions.

According to one or more embodiments of the present invention, the composition is provided in a plastic or glass propellant free foaming dispenser and forms a breakable or collapsible foam when dispensed from the propellant free foaming dispenser.

According to one or more embodiments of the present invention, the composition further includes a liquefied or compressed gas propellant, for example, at a concentration of about 3% to about 25% of the total composition.

According to one or more embodiments of the present invention, the foamed composition has specific gravity of about 0.02 gr/ml to about 0.35 gr/ml.

According to one or more embodiments of the present invention, iodine is selected from molecular iodine and complexed iodine. Complexed iodine may be selected from cadexomer-iodine, diiodhydrin, domiodol, hydriodic acid, iodinated glycerol, iodoform, iodide and povidone-iodine According to one or more embodiments of the present invention, the solvent is water or a water miscible organic solvent, such as a polyhydroxy compounds and poly-ethoxylated compounds. In one embodiment the composition has a water-to-water miscible organic solvent ratio of about 1:10 to about 10:1. Due to the skin irritability of lower alkyl alcohols, the water miscible compound is not a lower alkyl, e.g., $C_1$-$C_5$, alcohol.

In one or more embodiments, the polyhydroxy compound is selected from ethylene glycol, propylene glycol, glycerol, butanediols and isomers thereof, pentaerythritol, sorbitol, mannitol, dimethyl isosorbide, polyethylene glycol, polypropylene glycol, diethylene glycol monoethyl ether and mixtures thereof.

In one or more embodiments, the poly-ethoxylated compound is selected from polyethylene glycol, tetrahydrofurfuryl alcohol and polyethyleneglycol. The solvent can be mixtures of water, polyhydroxy compounds and/or poly-ethyoxylated compounds.

According to one or more embodiments, a surface active agent may be an anionic surface active agent, a cationic surface active agent, a nonionic surface active agent, a zwitterionic surface active agent, an amphoteric surface active agent, an ampholytic surface active agent and mixtures thereof.

In one or more embodiments, the surface-active agent includes at least a non-ionic agent. In one or more embodiments, the surface active agent is a mixture of a non-ionic surface active agent and an anionic surface active agent provided at a weight ratio of about 4:1 to about 1:4 more preferably a weight ratio of about 2:1 to about 1:2. In one or more embodiments, the surface-active agent has a HLB value higher than about 8.

According to one or more embodiments, the foam adjuvant is selected from a fatty alcohol, a fatty acid mixtures thereof, and is provided at a concentration between about 0.4% and about 2.5% of the composition.

Another aspect the present invention provides a method of treating, alleviating or preventing a human or veterinary disorder by topically administering to a surface afflicted with the disorder an effective amount of the composition according to one or more embodiments of the present invention.

The method of the invention, according to one or more embodiments, provides for the prophylaxis, or treatment of or alleviation of the symptoms of a variety of infectious dermatological disorders, including for example heat burns, chemical burns, infections, wounds, cuts and ulcers and radioactive radiation damage, and burns and infections resulting from chemical and biological warfare agents.

BRIEF DESCRIPTION OF THE DRAWING

The invention is described with reference to the Figure, which is provided for the purpose of illustration only and is not intended to be limiting of the invention.

The Figure is an illustration of a foam dispenser used in one or more embodiments of the present invention.

DETAILED DESCRIPTION OF THE INVENTION

Composition

Figure 1:
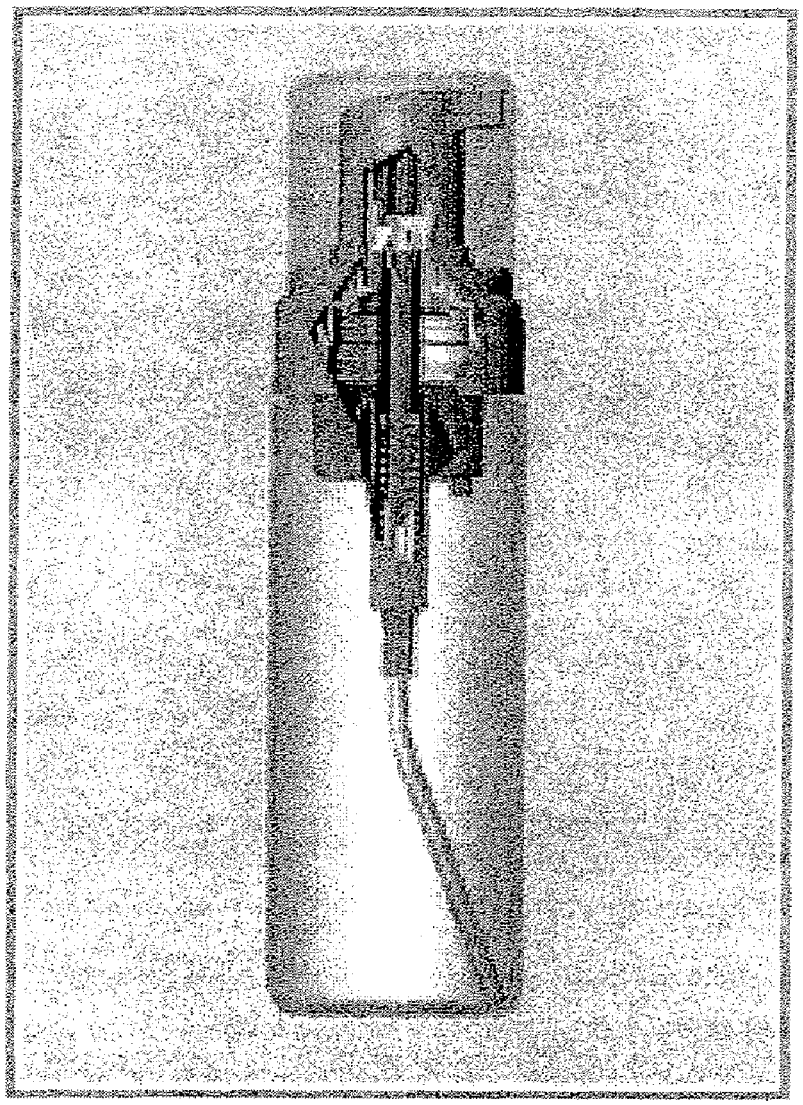

According to one aspect, the present invention provides a foamable composition of matter includes iodine, water, a foam adjuvant, a surface active agent and a gelling agent, in the following concentrations, reported as percent by weight:
 iodine: about 0.1% to about 5%;
 at least one solvent: about 80% to about 99.6%;
 at least one foam adjuvant: about 0.1% to about 5%;
 at least one surface active agent: about 0.1% to about 5%; and
 at least one gelling agent: about 0.1% to about 5%.
The % values presented herein are provided on a weight (w/w) basis of the total composition.

The composition according to one or more embodiments of the present invention is applied to the surface as a foam. That is, the foamed composition is applied to the substrate and is not generated by rubbing or lathering. The foamed composition, according to one or more embodiments of the present invention, is dispensed from a glass or plastic container that dispenses foam in the absence of a gas or liquid propellant.

Alternatively, the composition of the present invention further includes a liquefied or compressed gas propellant at a concentration of about 3% to about 25% of the total composition. Examples of suitable propellants include volatile hydrocarbons such as butane, propane, isobutane or mixtures thereof, and fluorocarbon gases.

The foamed composition, according to one or more embodiments of the present invention, is of exceptionally low specific gravity, for example, the foamed composition has a specific gravity in the range of about 0.02 gr/ml to about 0.35 gr/ml. Although of low specific gravity, the foam is highly stable and will remain without collapse for several minutes. Nonetheless, the foam collapses readily upon application of mild shear stress. Low specific gravity, high foam stability and ready collapsibility all contribute to a foamed composition that is easily applied and administered over large areas without rubbing or chaffing of the affected area.

Iodine

"Iodine" and "iodine species" include iodine in its native form or released from a compound. In its native form, iodine ($I_2$) is provided as bluish-black crystals, having density of about 5 g/cm$^3$. When used as is, the iodine concentration in the total composition ranges between 0.1% and 5% and more preferably, between 0.5% and 1.5%. In other embodiments of the present invention molecular iodine is released from an iodine-containing and/or producing compound. Non-limiting examples of such compounds include cadexomer-iodine, diiodhydrin, domiodol, hydriodic acid, iodinated glycerol, iodide, iodoform, and povidone-iodine. When provided as an iodine-containing and/or producing compound, the compound concentration in the total composition is calculated to achieve a final iodine concentration ranging between about 0.1% and 5% by weight and more preferably, between about 0.5% and about 1.5% by weight.

Solvent

According to one or more embodiments, the composition includes about 80% to about 99.6% solvent, and typically includes water. Iodine is not highly soluble in water and thus, formulation stability and effectiveness is limited. In a one or more embodiments of the present invention, the solvent includes water and a water miscible organic solvent, which by way of non-limiting examples, is a polyhydroxy compound and/or a poly-ethoxylated compound.

Suitable polyhydroxy solvents (polyols) include small organic molecules having two or more hydroxy groups on their carbon skeleton, such as ethylene glycol, propylene glycol, glycerol, butanediols and isomers thereof, pentaerythritol, sorbitol, mannitol, dimethyl isosorbide, polyethylene glycol, polypropylene glycol, diethylene glycol monoethyl ether (Transcutol®) and mixtures thereof.

Poly-ethoxylated compounds can enhance the effectiveness of iodine significantly by dissolving the $I_2$. Examples of suitable poly-ethoxylated compounds include polyethylene glycol (e.g., PEG 400), tetrahydrofurfuryl alcohol polyethyleneglycol ether (glycofurol, tetraglycol (TG)). Among the above-mentioned water miscible solvents, suitable compounds include transcutol, polyethylene glycol and TG and mixtures thereof. The ratio between water and the water miscible solvents is in the range of about 1:10 to about 10:1. In one or more embodiments, the ratio is between about 1:4 and about 4:1. Due to the skin irritability of lower alkyl (C1-C5) alcohols, and the tendency of such alcohols to impair the natural skin barrier by dissolving and removing the oily components of the skin, lower alkyl alcohols are not included as a miscible organic solvent.

Foam Adjuvant

A foam adjuvant is included in the composition to improve the stability and reduce the specific gravity of the foamed composition. In one or more embodiments of the present invention, foam adjuvants include fatty alcohols, fatty acids, and mixtures thereof. The foam adjuvant can include at least one fatty alcohol and at least one fatty acid.

Suitable fatty alcohols include alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). The concentration of the fatty alcohol required to support the foam system is inversely related to the length of its carbon chains. Fatty alcohols that are derived from beeswax, including a mixture of alcohols, a majority of which has at least 20 carbon atoms in their carbon chain, are especially well suited as foam adjuvants according to the present invention. The concentration of the fatty alcohol required to support the foam system is inversely related to the length of its carbon chains.

Suitable fatty acids include acids having 16 or more carbons in its carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the concentration of fatty acids required to support the foam system is inversely proportionate to carbon chain length.

Optionally, the carbon atom chain of the fatty alcohol or the fatty acid may have at least one double bond. A further class of foam adjuvant agent includes a long chain fatty alcohol or fatty acid, wherein the carbon atom chain is branched. The carbon chain of the fatty acid or fatty alcohol can be substituted with a hydroxyl group, such as 12-hydroxy stearic acid.

The foam adjuvant of the present invention may include a mixture of fatty alcohols, fatty acids and hydroxy fatty acids and alcohols in any proportion. The total amount of foam adjuvants is about 0.1% to about 5% (w/w) of the carrier mass, and typically, the total amount is about 0.4% to about 2.5% (w/w) of the carrier mass.

In one or more embodiments of the present invention, a fatty alcohol possesses a therapeutic properties per se. Long chain saturated and mono unsaturated fatty alcohols, e.g., stearyl alcohol, erycyl alcohol, arachidyl alcohol and docosanol have been reported to possess antiviral, anti infective, anti-proliferative and anti-inflammatory properties (U.S. Pat. No. 4,874,794). Longer chain fatty alcohols, e.g., tetracosanol, hexacosanol, heptacosanol, octacosanol, triacontanol, etc. are also known for their metabolism modifying properties and tissue energizing properties. Long chain fatty acids have also been reported to possess anti-infective characteristics. Thus, the iodine foamable composition of the present invention, containing the foam adjuvant provides a synergistic therapeutic benefit in comparison with currently used vehicles, which are inert and non-active.

Surface-active Agent

According to one or more embodiments of the present invention, the surface-active agent includes any agent linking oil and water in the composition, e.g., the agent can be a surfactant. In one or more embodiments of the present invention, the composition includes about 0.1% to about 5% of the surface-active agent.

Suitable surface-active agents include anionic, cationic, nonionic, zwitterionic, amphoteric and ampholytic surfactants, as well as mixtures of these surfactants. Such surfactants are well known to those skilled in the pharmaceutical and cosmetic formulation art. Non-limiting examples of useful surfactants include sucrose esters, sorbitan esters, PEG esters or ethers of fatty chains, mono or diglycerides, isoceteth-20, sodium methyl cocoyl taurate, sodium methyl oleoyl taurate, sodium lauryl sulfate, triethanolamine lauryl sulfate and betaines (e.g., cocamidopropyl betaine and lauramidopropyl betaine), which are known to contribute to foam stability (foam boosters).

While any surface-active agent may be used in the present invention, a surface-active agent having an HLB (hydrophilic-lipophilic balance) higher than 8 is used in one or more embodiments of the present invention.

Non-ionic surfactants are particularly well suited as surface-active agents. A combination of a non-ionic surfactant and an anionic surfactant (such as sodium lauryl sulfate) may also be used. A ratio of non-ionic surfactant to anionic surfactant between around 4:1 and about 1:4, or between about 2:1 and about 1:2, provides a foam, which upon rubbing onto the skin collapses easily, to allow facile spreading and absorption. A surface-active agent mix is even further improved when a foam stabilizing surfactant, such as cocamidopropyl betaine, is added.

Gelling Agent

In one or more embodiments of the present invention, the composition includes about 0.1% to about 5% of a gelling agent. Suitable gelling agents include, in a non-limiting manner, naturally-occurring polymeric materials such as locust bean gum, guar gum, sodium alginate, sodium caseinate, egg albumin, gelatin agar, carrageenin gum, sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), hydroxypropyl guar gum, soluble starch, cationic celluloses, cationic guars and the like and synthetic polymeric materials such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Also useful herein are gelling agents such as the acrylic acid/ethyl acrylate copolymers and the carboxyvinyl polymers sold, for example, by the B.F. Goodrich Company under the trademark of Carbopol® resins. These resins include a colloidal water-soluble polyalkenyl polyether cross linked polymer of acrylic acid cross linked with from 0.75% to 2% of a cross linking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid cross linked with about 1% of polyallyl ether of sucrose having an average of about 5.8 allyl groups for each sucrose molecule.

Methods of Evolving and Releasing the Foam

Any customary method of evolving foam is applicable according to the present invention. By way of example, in one optional configuration, the composition according to one or more embodiments of the present invention is preferably placed, together with a liquefied or compressed gas propellant in the amount of about 3% to about 25% of the total composition, in an aerosol container. Upon pressing the actuator, a breakable foam, suitable for topical administration is released. Due to the oxidizing nature of iodine, containers that are coated with highly durable lacquers of coatings are used.

In an alternative exemplary configuration, the composition according to one or more embodiments of the present invention is placed in a plastic or glass container, equipped with a foaming dispenser that works without gas propellants. Such dispensers are described, for example, in U.S. Pat. No. 6,536,629, in which the dispenser includes a container and a dispensing assembly coupled in liquid-tight manner. The dispensing assembly can have a liquid pump with a liquid inlet and a liquid outlet. An exemplary foam dispenser is shown in the Figure.

Foam Characteristics

The foam that is released from the aerosol container or from the propellant-free foaming dispenser is well aerated. It has specific gravity of about 0.02 gr/ml to about 0.35 gr/ml. When applied onto a surface, specifically a skin surface, and rubbed gently, it spreads easily over the area, without the need of extensive rubbing.

A foam composition of one or more embodiments of the present invention is advantageous over formulation options. A foamed composition may possess one or more of the following properties. The foam is lightweight and thus, economical. The foam is easily spreadable, allowing treatment of large areas such as the arms, back, legs and the breast. The flow properties provide a foam that spreads effectively into folds and wrinkles, providing uniform distribution of the active agent without the need of extensive rubbing and absorbs into the skin. The low specific gravity, e.g., fluffy, nature of the foam renders application of the foam on large skin areas very easy, irritation-free and painless.

Foam Applications

The compositions according to one or more embodiments of the present invention are useful in the various medicinal disciplines including human and veterinary medicine. More generally, the compositions according to the present invention can be used in situations where use of iodine is preferred including, but not limited to, medicine, industrial processes, diagnostics and environmental purposes.

Specifically, the compositions according to one or more embodiments of the present invention are useful as antiseptic compositions. The compositions may be further used to protect from, prevent, alleviate the symptoms of or cure a variety of infectious dermatological disorders, including: bacterial Infections including cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, erythrasma; fungal infections including dermatophyte infections, yeast infections; parasitic infections including scabies, pediculosis, creeping eruption and viral infections.

The treatment of heat burns, chemical burns (caused by chemicals such as acids, bases, caustic materials and warfare chemicals), wounds, cuts and ulcers using the composition according to one or more embodiments of the present invention is particularly advantageous. Upon application, the foam spreads easily, covering the surface of the affected area, and without causing pain.

The composition of the invention is also useful as a protectant in case of exposure to radiation and radioactive isotopes.

According to another aspect the present invention provides a method of treating, alleviating or preventing a human or veterinary disorder by topically administering to a surface afflicted with the disorder an effective amount of the composition including:
about 0.1% to about 5% by weight iodine;
about 80% to about 99.6% by weight of at least one solvent;
about 0.1% to about 5% by weight of at least one foam adjuvant;
about 0.1% to about 5% by weight of at least one surface active agent; and
about 0.1% to about 5% by weight of at least one gelling agent.

The present invention provides for the prophylaxis, or treatment of or alleviating the symptoms of a variety of infectious dermatological disorders, including heat burns, chemical burns, infections, wounds, cuts and ulcers and radioactive radiation damage, and burns and infections resulting from chemical and biological warfare agents.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Foamable Iodine Composition

The table below lists the components of the foamable composition.

| Ingredient | % (w/w) | Function |
|---|---|---|
| Iodine (I$_2$) | 1% | Active agent |
| Purified Water | 64.3% | Water |
| Glycofurol | 30% | Water miscible solvent |
| Stearyl alcohol | 1% | Foam adjuvant |
| Sodium Lauryl Sulfate | 1% | Surface active agent |
| Sucrose Ester 70 | 1% | Surface active agent |
| Cocamidopropyl Betaine | 0.5% | Surface active agent |
| Methocel LV15 (Hydroxypropylmethyl cellulose) | 0.8% | Gelling agent |
| Xanthan Gum | 0.4% | Gelling agent |

Iodine was dissolved in a mixture of glycofurol and stearyl alcohol and the mixture was heated to ~60 C until homogeneity was obtained. Methocel was dispersed in one third portion of water, preheated to 80° C., and sucrose ester was added. The remaining two-third portion of water at room temperature was added under vigorous stirring; and xanthan gum and sodium lauryl sulfate and cocamidopropyl betaine were added mixing continuously for 15 minutes under vigorous stirring. The iodine mixture was added carefully to aqueous mixture and was stirred for an additional 5 minutes for complete homogeneity. The resultant product was cooled to room temperature and filled into bottles.

EXAMPLE 2

Pressurized Foam Comprising Iodine

The composition of Example 1 (50 ml) at ambient temperature was added to a 125 ml aerosol container, the container was sealed with an aerosol valve and a butane/propane propellant (about 16% of the composition mass) was compressed into the container. Upon pressing the aerosol valve, a rich foam having specific gravity of about 0.1 gr/ml was released.

EXAMPLE 3

Iodine Non-Pressurized Foam

The composition of Example 1 (50 ml) at ambient temperature was added to a 125 ml container, equipped with a foaming dispenser that works without gas propellants (Airspray International Inc., 3768 Park Central Blvd. North, Pompano Beach, Fla. 33064, USA). Upon pressing the aerosol valve, rich foam having specific gravity of about 0.1 gr/ml to about 0.3 gr/ml was released.

What is claimed is:
1. A method of treating or alleviating a dermal or mucosal condition selected from the group consisting of wounds, burns, infections, ulcers and combinations thereof, comprising
   a. releasing an effective amount of non-irritating foamable composition from an aerosol container comprising:
      i. about 0.1% to about 5% by weight of iodine;
      ii. about 80% to about 99.6% by weight of at least one solvent;
      iii. about 0.1% to about 5% by weight of at least one foam adjuvant,
      wherein the at least one foam adjuvant is selected from a fatty alcohol, a fatty acid and a hydroxy fatty acid and mixtures thereof;
      iv. about 0.1% to about 5% by weight of at least one surface active agent; and
      v. a liquefied or compressed gas propellant wherein the weight ratio of the propellant to the remainder of the composition is about 3:97 to about 25:75, and wherein upon release, the foamable composition forms a thermally stable breakable foam having a specific gravity of between about 0.02 g/mL and about 0.35 g/mL;

b. applying the breakable foam to an afflicted surface having a dermatological or mucosal disorder; and c. collapsing the breakable foam by applying a gentle rub, wherein the collapsed foam is absorbed into the afflicted surface without chaffing of the surface.

2. The method of claim 1, wherein the composition is provided in a plastic or glass dispenser.

3. The method of claim 1 wherein the iodine is selected from native iodine and complexed iodine.

4. The method of claim 3 wherein the complexed iodine is selected from cadexomer-iodine, diiodhydrin, domiodol, hydriodic acid, iodinated glycerol, iodoform, and povidone-iodine.

5. The method of claim 1, wherein the at least one solvent comprises water.

6. The method of claim 5, further comprising a water miscible organic solvent.

7. The method of claim 6, wherein the water miscible organic solvent is selected from a polyhydroxy solvent and a poly-ethoxylated compound.

8. The method of claim 7, wherein the polyhydroxy solvent is selected from the group consisting of ethylene glycol, propylene glycol, glycerol, butanediols and isomers thereof, pentaerythritol, sorbitol, mannitol, dimethyl isosorbide, polyethylene glycol, polypropylene glycol, diethylene glycol monoethyl ether and mixtures thereof.

9. The method of claim 7, wherein the poly-ethoxylated compound is selected from the group consisting of polyethylene glycol, tetrahydrofurfuryl alcohol and polyethyleneglycol.

10. The method of claim 6, having a water to water miscible organic solvent ratio of about 1:10 to about 10:1.

11. The method of claim 1, wherein the at least one surface active agent is selected from the group consisting of anionic surface active agents, cationic surface active agents, nonionic surface active agents, zwitterionic surface active agents, amphoteric surface active agents, ampholytic surface active agents and mixtures thereof.

12. The method of claim 11, wherein the at least one surface-active agent is a mixture of a non-ionic surface-active agent and an ionic surface-active agent.

13. The method of claim 12, wherein the non-ionic surface active agent to ionic surface active agent weight ratio is in the range of about 4:1 to about 1:4.

14. The method of claim 12, wherein the non-ionic surface acting agent to ionic surface active agent weight ratio is in the range of about 2:1 to about 1:2.

15. The method of claim 11, wherein the at least one surface-active agent has a HLB value higher than about 8.

16. The method of claim 1, wherein the at least one foam adjuvant concentration is between about 0.4% and about 2.5% of the composition.

17. The method of claim 1, wherein the infection is selected from a bacterial infection, a fungal infection and a viral infection.

18. The method of claim 17, wherein the bacterial infection is selected from cellulitis, acute lymphangitis, lymphadenitis, erysipelas, cutaneous abscesses, necrotizing subcutaneous infections, staphylococcal scalded skin syndrome, furuncles, impetigo, hidradenitis suppurativa, carbuncles, paronychial infections and erythrasma.

19. The method of claim 18, wherein the bacterial infection is selected from a dermatophyte infections and a yeast infection.

20. The method of claim 1, wherein the condition is related to radiation or radioisotope exposure.

21. The method of claim 1, wherein the condition is related to chemical or biological warfare.

22. The method of claim 1, wherein the composition further comprises about 0.1% to about 5% by weight of at least one gelling agent.

23. The method of claim 22, wherein the at least one gelling agent comprises naturally-occurring polymeric materials, chemically modified starches, semi-synthetic polymeric materials, synthetic polymeric materials, acrylic acid/ethyl acrylate copolymers and carboxyvinyl polymers.

24. The method of claim 22, wherein the at least one gelling agent comprises locust bean gum, guar gum, sodium alginate, sodium caseinate, egg albumin, gelatin agar, carrageenin gum, sodium alginate, xanthan gum, quince seed extract, tragacanth gum, starch, a cellulose ether, hydroxypropyl guar gum, soluble starch, cationic cellulose, cationic guar, a carboxyvinyl polymer, polyvinylpyrrolidone, polyvinyl alcohol, a polyacrylic acid polymer, a polymethacrylic acid polymer, a polyvinyl acetate polymer a, a polyvinyl chloride polymer, a polyvinylidene chloride polymer, a polyalkenyl polyether cross-linked polymer of acrylic acid, or a mixture thereof.

25. The method of claim 22, wherein the at least one gelling agent comprises hydroxypropylmethyl cellulose, hydroxyethyl cellulose, methyl cellulose, carboxymethyl cellulose, or a mixture thereof.

* * * * *